United States Patent
Alakhov et al.

(10) Patent No.: US 8,389,558 B2
(45) Date of Patent: Mar. 5, 2013

(54) BENDAMUSTINE AMPHIPHILIC ANIONIC COMPOSITIONS

(75) Inventors: Valery Alakhov, Ile Bizard (CA); Grzegroz Pietrzynski, Montreal (CA); Patel Kishore, Pierrefonds (CA); Thomasz Popek, Pointe-Claire (CA)

(73) Assignee: Supratek Pharma Inc., Montreal (CA)

( * ) Notice: Subject to any disclaimer, the term of this patent is extended or adjusted under 35 U.S.C. 154(b) by 0 days.

(21) Appl. No.: 12/838,928

(22) Filed: Jul. 19, 2010

(65) Prior Publication Data

US 2011/0015244 A1  Jan. 20, 2011

Related U.S. Application Data

(60) Provisional application No. 61/271,345, filed on Jul. 20, 2009.

(51) Int. Cl.
*A61K 31/415* (2006.01)
(52) U.S. Cl. ........ 514/394; 514/393; 514/385; 514/359; 548/304.4; 548/302.7; 548/301.7; 548/300.1
(58) Field of Classification Search .................. None
See application file for complete search history.

(56) References Cited

U.S. PATENT DOCUMENTS

| | | | | |
|---|---|---|---|---|
| 2,731,338 A | * | 1/1956 | Fike et al. ............... | 504/317 |
| 5,444,078 A | * | 8/1995 | Yu et al. .................. | 514/372 |
| 6,136,836 A | * | 10/2000 | Bettarini et al. ......... | 514/394 |
| 6,407,079 B1 | | 6/2002 | Muller et al. | |
| 6,583,125 B2 | | 6/2003 | Rubinfeld | |
| 6,624,141 B1 | | 9/2003 | Yang et al. | |
| 2006/0128777 A1 | * | 6/2006 | Bendall et al. .......... | 514/394 |
| 2006/0142234 A1 | * | 6/2006 | Chen et al. .............. | 514/44 |
| 2006/0159713 A1 | | 7/2006 | Brittain et al. | |
| 2008/0299166 A1 | | 12/2008 | Szente et al. | |
| 2010/0125089 A1 | * | 5/2010 | Soll et al. ............... | 514/303 |
| 2010/0179198 A1 | * | 7/2010 | Mertoglu et al. ........ | 514/355 |

FOREIGN PATENT DOCUMENTS

| | | |
|---|---|---|
| CA | 2593582 A1 | 7/2006 |
| CA | 2679919 A1 | 9/2008 |
| CN | 1846685 A | 10/2006 |
| CN | 101219113 A | 7/2008 |
| CN | 101606934 A | 12/2009 |

OTHER PUBLICATIONS

"The Hydrocarbon/Water Interfacial Behaviour of Alkyl Aryl Sulfonates" by Singh, Lubric. Sci. 13, 91-101 (2000).*
Chatterji et al., "Kinetick of Chlorambucil Hydrolysis Using High-Pressure Liquid Chromatography", J Pharm Sci 71 (1):50-54 (1982).
Evjen, T.J., "Developments of Improved Bendamustin-Liposomes", Thesis for the degree of Master of Pharmacy, Department of Pharmaeutics and Biopharmaceutics, Institute of Pharmacy, Faculty of Medicine, University of Tormso (2007).
Haase et al., "Untersuchungen zur Plasmaeiweiβbindung von Bendamustin (Cytostasan(R)) and Ambazon", Z. Klin. Med. 45(14):1267-1271 (1990).
Maas et al., "Stabilitat von Bendamustinhydrochlorid in Infusionsloungen", Die Pharmazie 49:775-777 (1994 ).
Meyer-Losic et al., "DTS-108, A Novel Peptidic Prodrug fo SN38; In vivo Efficacy and Toxicokinetic Studies", Clin Cancer Res 14(7):2145-2153 (2008).
Pencheva et al., HPLC Study on the stability of bendamustine hydrochloride immobilized onto polyphosphoesters, J Pharm Biomed Anal (2008) doi:10.1016/j.pba.2008.09.001.
Preiss et al., "Untersuchungen zur Pharmakokinetik von Bendamustin (Cytostasan(R)) am Menschem", Pharmazie 40:782-784 (1985).
Teichert et al., "Characterization of two phase I metabolites of bendamustine in human liver microsomes and in cancer patients treated with bendamustine hydrochloride", Cancer Chemother Pharmacol 59:759-770 (2007).
www.accessdata.fda.gov/drugsatfda_docs/label/2008/022249lbl.pdf, (2008).
http://www.sigmaaldrich.com/catalog/product/SIGMA/B5437?lang=en&region=US—Sigma-Aldrich catalog—Bendamustine hydrochloride hydrate, (accessed Jun. 11, 2012).

* cited by examiner

*Primary Examiner* — Brandon Fetterolf
*Assistant Examiner* — Theodore R West
(74) *Attorney, Agent, or Firm* — Porzio, Bromberg & Newman, P.C.

(57) ABSTRACT

The present invention is directed to pharmaceutical compositions comprising bendamustine and one or more amphiphilic anionic compounds and self assembled aggregates, which aggregates exhibit enhanced stability in aqueous solutions, including plasma, are disclosed. The unexpectedly enhanced stability afforded by such aggregates permits patients to be treated with bendamustine in lower and/or with less frequent dosages or to improve its therapeutic effect while using the same as presently used treatment protocol.

8 Claims, No Drawings

BENDAMUSTINE AMPHIPHILIC ANIONIC COMPOSITIONS

CROSS REFERENCE TO RELATED APPLICATION

This application claims the benefit of U.S. Provisional Patent Application No. 61/271,345, filed Jul. 20, 2009, the entirety of which is hereby incorporated by reference into this application.

FIELD OF THE INVENTION

The present invention is directed to pharmaceutical compositions comprising bendamustine and amphiphilic anionic compounds, and in particular to an aggregate form of the composition comprising bendamustine and one or more amphiphilic anionic compounds, which aggregates exhibit enhanced stability in aqueous solutions, including plasma.

BACKGROUND OF THE INVENTION

Bendamustine, 4-[5-[Bis(2-chloroethyl)amino]-1-methyl-benzimidazol-2-yl]butanoic acid, is used in the treatment of leukemia and certain lymphomas. However, this compound has limited chemical stability in plasma, thereby requiring high or repeated doses in order to achieve a therapeutic effect. United States Patent Application Publication No. 2006/0159713 (Brittain et al.) indicates that, once reconstituted into aqueous solutions, bendamustine quickly degrades and must therefore be administered to patients as quickly as possible. Maas et al.; "Stabililitat von Bendamustinhydrochlorid in Infusionslosungen"; Pharmazie 49:775-7 (1994) discloses that bendamustine hydrochloride is stable for only 9 hours at 23° C. in saline solution.

Attempts have been made to increase the stability of bendamustine by complexing such molecule with polymeric materials. However, the approaches taken thus far have only achieved marginal success. Pencheva et al; "HPLC study on the stability of bendamustine hydrochloride immobilized onto polyphosphoesters; J. Pharma. Biomed. Anal; (2008) attempted to improve the stability of bendamustine by complexing such compound with polyphosphoesters. However, FIG. 2 of such article shows that even the most stable complex decreases by a full log point (90%) in about 45 minutes at pH 7.

Evjen; "Development of Improved Bendamustin-Liposomes"; Masters Thesis; University of Tromso (2007) employed dual asymmetric centrifugation to incorporate bendamustine into liposomes. According to Table 18 (on page 79), these formulations only provide a marginal increase of stability relative to free bendamustine (20 minutes half-life vs. 14 minutes half-life for free bendamustine).

Accordingly, there is a need for improved formulations of bendamustine which will provide enhanced stability in aqueous solutions.

SUMMARY OF THE INVENTION

The present invention is directed to pharmaceutical compositions comprising bendamustine and one or more amphiphilic anionic compounds. The compositions self-assemble in an aqueous media to form an aggregate, which aggregates exhibit enhanced stability in aqueous solutions, including plasma. The compositions may further comprise pharmaceutically acceptable excipients, such as sugars, polyalcohols, soluble polymers, salts and lipids. The compositions are suitable for injection or infusion into patients in need for treatment with bendamustine. The unexpectedly enhanced stability afforded by such aggregates permits patients to be treated with bendamustine in lower and/or with less frequent dosages or to improve its therapeutic effect while using the same as presently used treatment protocol.

DETAILED DESCRIPTION

The present invention is directed to compositions comprising bendamustine and one or more amphiphilic anionic compounds. The composition forms self-assembled aggregates in aqueous media, which aggregates exhibit enhanced stability in aqueous solutions, including plasma.

As is employed herein, the term "amphiphilic" refers to a compound which has at least one hydrophilic moiety and at least one hydrophobic moiety.

The hydrophilic moiety of the amphiphilic compounds useful in the practice of this invention preferably comprises one or more sulphate and/or sulfonate anionic groups. Such anionic groups are typically in the form of pharmaceutically acceptable salts. It is preferred that the salts are sodium, magnesium, calcium, or ammonium salts.

The hydrophobic moiety of the amphiphilic compounds useful in the practice of this invention comprises a hydrocarbon chain. The chain may be an aliphatic chain, or a mixed aliphatic-aromatic chain. The aliphatic chain can be linear or branched although it is preferred that the chain is linear.

The amphiphilic anionic compound may comprise one or more anionic groups per molecule. The ratio of the total number of anionic groups to the total number of carbon atoms is generally between about 1:4 and about 1:30. It is preferred that the ratio of anionic groups to the total number of carbon atoms is between about 1:8 and 1:18.

The anionic group may be directly attached to the hydrocarbon chain. Alternatively, the anionic group may be attached to the hydrocarbon chain by a linker.

Accordingly, in one embodiment, the amphiphilic anionic compound comprises a sulfonate group attached directly to an aliphatic hydrocarbon chain. Preferably, the anionic agent is an alkanesulfonate. In a preferred embodiment, the hydrocarbon chain of the alkanesulfonate contains between 10 and 18 carbon atoms.

In another embodiment, the amphiphilic anionic compound comprises a sulfonate group attached directly to an aromatic ring. Preferably, in this embodiment, the amphiphilic anionic compound is an alkylbenzenesulfonate. In a more preferred embodiment, the alkyl chain of such alkylbenzenesulfonate contains between 8 and 14 carbon atoms. A particularly preferred amphiphilic anionic compound is dodecylbenzenesulfonate.

In yet another embodiment, the amphiphilic anionic compound comprises a sulfate group attached directly to an aliphatic chain. The amphiphilic anionic compound may be an alkyl sulfate. In a preferred embodiment, the alkyl fragment in the amphiphilic anionic compound is linear 1-hydroxyalkane composed of between 10 and 18 carbon atoms. Particularly preferred amphiphilic anionic compounds are dodecyl sulfate and tetradecyl sulfate. Another particularly preferred amphiphilic anionic compound is Caeliferin A.

In another embodiment, the amphiphilic anionic compound is a polysulfonated polyethylene, wherein the molecular weight of such polymer is about 100,000 Daltons or less.

In a further embodiment, the amphiphilic anionic compound is a polysulfated polyethylene polyol, wherein the molecular weight of such polymer is about 100,000 Daltons or less.

In another embodiment, the amphiphilic anionic compound is a hydrophobically modified polysulfated polysaccharide.

In one embodiment, the linker is an ether comprising a chain of oxyethylene groups, oxypropylene groups, and/or oxybutylene groups. The total number of such groups in the chain is not more than 4. The amphiphilic anionic compound may be an alcohol ether sulfate. In a preferred embodiment, the alcohol in the agent is linear 1-hydroxyalkane composed of between 10 and 18 carbon atoms, and the ether is composed of 1, 2, or three oxyethylene groups.

In another embodiment, the linker is a sugar, or a polyol, linear or cyclic, comprising between 3 and 6 hydroxyl groups, where some of the hydroxyl groups are used to form ether or ester bonds to one or two hydrocarbon chains, and to one or two sulfate groups. It is preferred that each of said hydrocarbon chains contain between 8 and 18 carbon atoms.

In one preferred embodiment, the amphiphilic anionic compound is an O-sulfoglyceryl fatty acid ester.

In another preferred embodiment, the amphiphilic anionic compound is an O-sulfoglyceryl alkyl ether.

In another preferred embodiment, the amphiphilic anionic compound is an O-sulfosorbitan fatty acid ester.

In another preferred embodiment, the amphiphilic anionic compound is a glycolipid sulfate.

In another embodiment, the linker is an amide. In a preferred embodiment, the amphiphilic anionic compound is an amide of alkanoic acid and N-methyl-N-alkylsulfonic acid. A particularly preferred amphiphilic anionic compound is an amide of alkanoic acid comprising between 8 and 18 carbon atoms and N-methyl-taurine or N-methyl-3-aminopropylsulfonic acid. Particularly preferred amphiphilic anionic compounds are N-methyltaurolipids. Other particularly preferred amphiphilic anionic compounds are dialkyl sulfosuccinates.

It is known to those skilled in art that the anionic agents described above are usually manufactured not as unique chemical entities of exactly defined structure, but rather as mixtures of isomeric and homologous chemical compounds of related structures.

A mixture of one or more of the amphiphilic anionic compounds described above can be used to prepare the aggregates of the present invention.

The aggregates of the present invention are typically prepared by mixing the amphiphilic anionic compound with bendamustine. The anionic agent is a chemical, the molecules of which self-assemble to form aggregates in aqueous media. Such aggregates have lipophilic core and ionic outer layer.

The weight ratios of bendamustine to amphiphilic anionic compound may range from about 1:2 to about 1:1000; is preferably between about 1:5 and about 1:500; and is most preferably between about 1:10 and about 1:100.

As will be recognized by those of skill in the art, the concentration of the amphiphilic anionic compound must be at or above the critical micelle concentration during application. The critical micelle concentration will depend upon a number of factors, including the composition of the amphiphilic anionic compound, pH, ion strength, etc., but can easily be determined by routine experimentation for any given composition employing procedures well known to one of skill in the art.

The compositions of this invention may further contain pharmaceutically acceptable excipients, such as sugars, polyalcohols, soluble polymers, salts and lipids.

Sugars and polyalcohols which may be employed include, without limitation, lactose, sucrose, mannitol, and sorbitol.

Illustrative of the soluble polymers which may be employed are polyoxyethylene, poloxamers, polyvinylpyrrolidone, and dextran.

Useful salts include, without limitation, sodium chloride, magnesium chloride, and calcium chloride.

Lipids which may be employed include, without limitation, fatty acids, glycerol fatty acid esters, glycolipids, and phospholipids.

Compositions of bendamustine and amphiphilic anionic compounds may disperse and release the drug upon dilution in aqueous media.

The composition of bendamustine with amphiphilic anionic compounds renders the bendamustine sufficiently chemically stable.

The compositions of the present invention are suitable for injection or infusion into patients in need for treatment with bendamustine.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

EXAMPLES

Example 1

Preparation of Bendamustine Composition Comprising Sodium Dodecyl Sulfate 1 g Sodium dodecyl sulfate was dissolved in 100 mL water. This solution was used to dissolve solid mixture of 60 mg of bendamustine and 102 mg of D-mannitol. The composition was thoroughly mixed.

Example 2

Bendamustin Chemical Stability in Various Formulations Comprising Amphilphilic Anionic Agents and Phosphate Buffer Formulations were prepared by dissolving bendamustine hydrochloride in pre-equilibrated 1% (w/v) aqueous solution of amphiphilic anionic agent containing 6 mM phosphate buffer, pH 7.2. The final concentration of bendamustine was 0.6 mg/mL. The formulations were incubated at 25° C., and were periodically analyzed by HPLC as follows. 10 μL samples were separated using Waters SymmetryShield RP-18 3.5 μm column (4.6×50 mm) at the flow of 1.5 mL/min of acetonitrile-water gradient containing 0.1% TFA. Peak detection has been performed with means of UV absorption detection at 260 nm. The area of the peak of Bendamustine was used to evaluate the rate of drug decomposition in the first order kinetics model.

The results expressed as decomposition half times (T½) are presented in Table 1 below.

TABLE 1

| Amphiphilic anionic agent | T½ |
|---|---|
| Control (phosphate buffer) | 44 min |
| Sodium 3-[(3-Cholamidopropyl)dimethylammonio]-1-Propanesulfonate 1% | 92 min |
| Sodium N-lauroylsarcosinate 1% | 102 min |

TABLE 1-continued

| Amphiphilic anionic agent | T½ |
|---|---|
| Sodium dodecyl sulfate 1% | 806 min |
| Sodium dodecylbenzylsulfonate 1% | 1354 min |

The above results show the unexpected stability exhibited by the aggregates of this invention.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A composition comprising bendamustine and an amphiphilic anionic compound, wherein the amphiphilic anionic compound is an alkylbenzenesulfonate or an alkyl sulfate.

2. The composition of claim 1 wherein the weight ratio of bendamustine to amphiphilic anionic compound is between about 1:2 and about 1:1000.

3. The composition of claim 1 wherein the weight ratio of bendamustine to amphiphilic anionic compound is between about 1:5 and about 1:500.

4. The composition of claim 1 wherein the weight ratio of bendamustine to amphiphilic anionic compound is between about 1:10 and about 1:100.

5. The composition of claim 1 wherein the amphiphilic anionic compound is dodecylbenzenesulfonate.

6. The composition of claim 1 wherein the amphiphilic anionic compound is selected from the group consisting of dodecyl sulfate and tetradecyl sulfate.

7. The composition of claim 1 wherein the composition is a self assembled aggregate.

8. The composition of claim 1 wherein the composition is a pharmaceutical composition.

* * * * *